United States Patent [19]
Lugnani et al.

[11] Patent Number: 5,843,016
[45] Date of Patent: Dec. 1, 1998

[54] ELECTROMOTIVE DRUG ADMINISTRATION FOR TREATMENT OF ACUTE URINARY OUTFLOW OBSTRUCTION

[75] Inventors: Franco Lugnani, Trieste, Italy; Manfred Stöhrer, Murnau; Augustinus Kramer, Ohlstadt, both of Germany; Robert L. Stephen, Salt Lake City, Utah; Umberto Fontanella, Milan, Italy; Cino Rossi, Rome, Italy; Silvio Eruzzi, Mantova, Italy

[73] Assignee: Physion S.r.L., Mirandola, Italy

[21] Appl. No.: 617,143

[22] Filed: Mar. 18, 1996

[51] Int. Cl.⁶ ........................................ A61N 1/30
[52] U.S. Cl. .............................. 604/21; 604/54
[58] Field of Search ................. 604/21, 28, 49, 604/54–5; 607/3, 40–41, 72, 75, 115–16, 143

[56] References Cited

U.S. PATENT DOCUMENTS

| | | | |
|---|---|---|---|
| 5,232,441 | 8/1993 | Stephen et al. | 604/21 |
| 5,301,688 | 4/1994 | Stephen et al. | 604/20 |
| 5,401,239 | 3/1995 | Stephen et al. | 604/21 |
| 5,486,160 | 1/1996 | Rossi et al. | 604/21 |

OTHER PUBLICATIONS

Fontanella, U.A., et al, "Iontophoretic Local Anaesthesia for Bladder Dilatation in the Treatment of Interstitialcystitis," Br. J. Urol, Jun. 1992, 69(6)662–663.

Ramani, A.J., et al. "A practical approach to the painful bladder syndrome," J. Reprod. Med. Obstet. Gynec. 1990 35(8) 805–809.

Nurmi, M., et al. "Evaluation of upper and lower urinary tracts after Camry operation," Scand. J. Urol. Nephrol. 1989 23(4) 275–277.

Lugnani, F., et al. "Iontophoresis of Drugs in the Bladder Wall:. Equipment and Prelim. Studies," Artif. Organs. 17(1)8–17, 1993.

*Primary Examiner*—Mark Bockelman
*Attorney, Agent, or Firm*—Jacobson & Johnson

[57] ABSTRACT

A method of treating acute urinary outflow system obstruction caused by disease of the prostate gland by localised electromotive drug administration. The treatment comprises insertion within the prostatic urethra and within the bladder cavity of a urethral catheter which incorporates a specific electrode and is adapted to perform the electromotive administration of a drug or drug mixture into diseased prostatic tissues thereby resolving the pathologies without resorting to surgery.

30 Claims, 2 Drawing Sheets

ELECTROMOTIVE DRUG ADMINISTRATION FOR TREATMENT OF ACUTE URINARY OUTFLOW OBSTRUCTION

BACKGROUND OF THE INVENTION

1. Field of the Invention

The present invention relates to electromotive drug administration for treatment of acute urinary outflow system obstruction and to a related device. In particular, this invention relates to a method and device for the treatment of acute urinary outflow system obstruction due to pathology of the prostate gland, by localised electromotive administration of drug(s) solution.

2. Description of the Relevant Art

The prostate, the largest accessory gland of the male reproductive tract, is about the size of a walnut in the young to middle-aged adult. Anatomically, it is a partly glandular and partly fibro-muscular organ which surrounds the prostatic section of the urethra and is itself enclosed by a dense fascial sheath.

The prostate gland is roughly conical in shape with a base, an apex and four surfaces: posterior, anterior and two inferolateral surfaces. The base of the prostate is related to the neck of the bladder wherein the anatomically ill-defined internal sphincter lies. The apex of the prostate is inferior and terminates just proximal to the sphincter urethrae (external sphincter), located at the distal end of the prostatic urethra.

The central zone is located at the base of the prostate, is traversed by the ejaculatory ducts and lies immediately posterior to the prostatic urethra. The peripheral zone comprises some 75% of the prostatic glandular tissue, proximally it surrounds the central zone and distally it expands laterally and inferiorly around the prostatic urethra. The transitional zone originates from the periurethral ducts, hypertrophies with advancing age and is the major site of prostatic adenoma or benign prostatic hypertrophy (BPH). It is distinguished by two lateral lobes and, at times, by a third median lobe. The anterior fibromuscular stroma surrounds the prostate gland and urethra anteriorly.

Anatomically, the central zone and the peripheral zone comprise the peripheral portion of the prostate gland while the transitional zone comprises the internal portion of the gland.

The internal sphincter, which is under the influence of the autonomic nervous system, extends from the bladder neck throughout the length of the prostatic urethra. Both the internal sphincter and the anterior fibromuscular stroma contain numerous adrenergic $\alpha_1$ receptors, the stimulation whereof causes contraction and the blocking whereof causes relaxation, of the internal sphincter and anterior fibromuscular stroma. A plurality of small ducts drain the prostate glandular tissue into the prostatic urethra. The prostate gland, which is small at birth, rapidly enlarges at puberty, then stabilises in size until about the mid-forties when, in most males, it progressively enlarges (hypertrophies). In a small minority the gland becomes more fibrous and smaller. The cause of these changes is not fully understood but is undoubtedly related to endocrine function. The prostate gland could be subjected to numerous pathologies which could lead to a partial or complete obstruction of urinary outflow.

Benign Prostatic Hypertrophy (BPH) affects a high proportion of older men and is a common cause of urethral obstruction which may lead to nocturia, dysuria, and urgency. The enlarged prostate gland, arising primarily from the transitional zone, may cause several different anatomical malformations, depending upon the circumstances such as increasing compression of the prostatic urethra, increasing constriction of the bladder neck and internal urethral orifice due to projection of the lateral lobes into the bladder cavity and projection of the median lobe into the bladder cavity, obstructing the internal urethral orifice by a ball-valve mechanism; and any combination of the above. The situation is further complicated by the fact that, depending upon the above conditions, the patient may have a small–medium (30 g–60 g) sized adenoma, a medium–large (60 g–90 g) adenoma or a very large (>90 g) adenoma.

Another disease affecting the gland is cancer of the prostate, 80% whereof forms in the peripheral gland and which is probably the most common tumour in men, being found microscopically at autopsy in 60% of men over 80 years of age. The fact that this finding is incidental emphasises the single most exasperating aspect of prostatic cancer: it may lie quiescent for years, possibly decades, and the subject dies of some other cause, or it may metastasise early in its course and, although initially responsive to hormonal therapy, the widespread secondary cancers eventually overwhelm the subject. As yet, there is no way to predict how a prostatic cancer will behave in a particular person so that, until recently, this situation left the medical profession with some unenviable choices: 1) radical surgery and/or radiotherapy, both of which are accompanied by permanent, severe morbidity in a high proportion of patients; 2) surgical or pharmacological castration; 3) do nothing. Recently, ablation of cancer in the prostate using cryotherapy (liquid N2) or laser is becoming more attractive, demonstrating reasonable results with minimum morbidity. Continuing expansion of an unrecognised prostatic cancer, superimposed upon BPH, also leads to acute urinary retention.

Infection of the prostate gland, although less common than BPH or cancer of the prostate, is significant because, being superimposed upon BPH, it often causes acute urinary retention and because the pain caused by this condition is frequently sufficiently severe to require hospitalisation. Also, prostatic infections, or at least the symptomatology thereof, can be extremely difficult to eliminate with the subject continually affected by chronic pain, tenderness and irritation. Whether this is due to a peculiar autoimmune effect or, more likely, to residual microorganisms sheltered from systemic antimicrobial therapy within small prostatic concretions ("privileged" sites) is unknown. What is known is that systemic antimicrobial therapy is often only partly successful in that acute symptoms disappear but chronic symptoms persist.

It is known that acute urinary retention due to prostatic disease almost always involves some degree of BPH. Most subjects are of advancing years and often provide a history of partial urinary retention: straining in order to void and voiding 2–3 times during normal sleeping hours (nocturia), indicating that a quantity of residual urine remains within the bladder.

Currently, following a clinical work-up of acute urinary retention due to B.P.H., which consists of history, physical examination, ultrasound of kidneys, bladder and prostate, various blood tests including one for PSA (Prostate Specific Antigen), ECG and chest X'Ray, there are three mainstays of therapy:

1. Catheterisation: insertion of a transurethral catheter and drainage of bladder contents brings immediate relief of the acute situation. Performed with care, this is usually a simple, painless procedure although it can be difficult on occasion and also very painful if an infective element is present. The catheter(s) is almost always left in situ as recurrence of acute urinary obstruction is very common.

The problem with this approach is that the presence of an indwelling catheter signals inevitable infection sooner or later; therefore, during this period antibiotics must be administered as a counter to infection, which still may occur due to invasion of resistant bacteria.

2. Operation: If the diagnosis is uncomplicated BPH, simple (i.e. not radical) prostatectomy is almost always advised within the next 48–72 hours, the rationale being that: it is not a really major procedure, there are few complications and the results are good and moreover there is no alternative other than a permanent indwelling catheter (s) with all the accompanying inconveniences and the inevitability of antimicrobial-resistant, and possibly life-threatening, infections within the bladder.

This therapeutic method is not devoid of serious drawbacks. In fact, although simple prostatectomy, whether performed by transurethral resection (TURP) or by laparotomy and transvesical or retropubic resection, does not constitute an invasive procedure comparable to many other surgical procedures, almost all of these patients are however of advancing years, their organ systems no longer possess the resilience of youth and finely judged, attentive anaesthesia is required. Moreover, patients' blood vessels are sclerotic to some degree and bleeding, sometimes profuse, always occurs and invariably the urologist understates the blood loss and intravenous fluid replacement is often inadequate. Post operatively, there is compensatory vasoconstriction (harmful) to counter the bleeding which continues for a further 24–48 hours. Furthermore, there is occasionally significant secondary hemorrhage 2–3 weeks post-operatively and the operation itself destroys the internal sphincter as a functional entity and there is a significant incidence of permanent incontinence. Urethral strictures occur in 3%–4% of patients, there is a small but definitive mortality attached to the procedure and some 6–12 months after prostatectomy there is an increased incidence of myocardial infarction ("heart attack") in prostatectomised patients as compared to matched controls.

3. A prolonged course of systemically administered α adrenergic blocking drugs: these agents relax the internal sphincter and so relieve the obstruction to some extent.

A prolonged course of systemically administered anti-androgenic drugs is also prescribed and these agents slowly bring about a degree of involution of BPH thereby relieving obstruction too. The time frame cannot be shortened by conventional means such as greatly increasing the systemic dose of α blockers and anti androgen drugs because the therapeutic ratio (benefits/severe side-effects) is too narrow. Also, the side-effects of prolonged administration of these drugs are not negligible. Moreover, systemic administration of almost all drugs results in only a small proportion of the drug actually reaching the specific site of pathology with therapeutic effect, whereas a large proportion is scattered throughout the body where the only effects are side-effects.

Localised (targeted) administration of drugs through the catheter is an attractive theoretical approach because of high concentrations attained at the sites of pathology and minimal systemic concentrations resulting in a virtual absence of side-effects.

Local administration and passive diffusion of drugs have not proven to be effective in the urinary tract because the urothelium, which lines the ureters, bladder and urethra, is the most impermeable of all mammalian plasma membranes and diffusion of drugs into underlying tissues approaches zero, therefore some additional force is required to breach this barrier. Finally, assuming that this force is made available, a redesign of catheters and associated equipment is required in order to direct the drugs into specific anatomic target sites: the bladder neck, the prostatic urethra and the hypertrophied prostate gland.

It is moreover known that EMDA comprises at least three important electrokinetic phenomena, which are: iontophoresis, electrophoresis and electroporation.

Iontophoresis is defined as the active transport of ionised molecules into tissues by application of an electric current through a solution containing the ions to be delivered. Quantitative values for the ionic flux (Ji) may be obtained by applying Faraday's Law as described by Banga et al. (Banga A. K., Chien Y. W. Iontophoretic Delivery of Drugs: Fundamentals, Developments and Biomedical Applications. J. Controlled Release 1988, 7, 1–24).

$$J_i = \frac{I}{|z| \cdot F}$$

The flux of a particular drug ion (dD/dt) in the solution of ions is expressed as $$dD/dt \text{ (moles/sec)} = \frac{I}{|z| \cdot F} \cdot t_r$$

where I is the electric current in amperes, $|z|$ is the absolute valence of the ion(s), F is Faraday's number and $t_r$, the transference number, reflects the proportion of current carried by the charged drug molecules and it varies inversely with the quantity, charge and mobility of all ions in solution, and is always < unity.

Transposing to the more clinically applicable milligrams (mg) and milliamperes ($I_m$)

$$dD/dt \text{ (mg/min)} = \frac{60 \cdot M \cdot I_m}{|z| \cdot F} \cdot t_r$$

where M is the molecular weight in daltons.

Electrophoresis, in accordance with Sibalis (U.S. Pat. No. 4,878,892), describes the transport of solutes associated with bulk movement of water. In an ionic liquid solution, iontophoresis induces transport of water (electro-osmosis) into underlying tissues which, in turn, induces an enhanced penetration of electrolytes down their coulombic gradients, of non electrolytes and even of electrolytes against their coulombic gradients as described by Petelenz et al. (Iontophoresis of dexamethasone: laboratory studies. J. Controlled Rel. 1992; 20: 55–66). Usually, iontophoresis dominates electrophoresis in terms of drug administration rates from a pure solution containing the drug in an ionised form. However, if the drug is present in low concentrations (usually <10-2 molar) and/or there is a rich admixture of extraneous ions, then the role of electrophoresis in the transport of the drug becomes increasingly important.

Electroporation, a term newly coined by Prausnitz et al., (Transdermal drug delivery by electroporation. Abstract Proceed. Intern. Symp.. Control. Rel. Bioact. Mat. 1992; 19) is used to outline a phenomenon known for many years and was described by Jung et al. in 1983 (Conformational requirements for the potential dependent pore formation of the peptide antibiotics alamethicin, suzukacillin and trichotoxin. In: Spach G ed. Physical Chemistry of Transmembrane Ion Motion. New York: Elsevier; 1983): Application of an electric field causes an increase in the permeability of biological membranes and thus there is increased transport of drugs down concentration gradients because the value of the diffusion coefficient (D) has been increased.

Thus, the three electrokinetic phenomena, iontophoresis, electrophoresis and electroporation are all involved in EMDA within the bladder and prostatic urethra. As stated herein above, iontophoresis is usually predominant when the drug ion to be administered is of the same polarity as the applied electrode but, if the concentration of the drug ion (and its counter ion) is too low to conduct the applied electric current effectively, then problems such as polarisation and hydrolysis of water become manifest. To counter these undesirable effects, additional extraneous electrolytes (often in the form of buffers) are usually added to the drug solution. These same electrolytes then act as charge competitors, reducing the iontophoretic rate of drug delivery while increasing electrophoretic transport rates, especially if these additional ions are carefully selected as described by Sibalis (U.S. Pat. No. 4,878,892). Extraneous ions are an inevitable accompanyment of EMDA within the bladder and prostatic urethra because of the continuous entry of electrolyte-rich urine, so that electrophoresis will always be involved. Excepting the specific conditions described by Prausnitz et al., the contribution supplied by electroporation to EMDA is generally unknown and is only mentioned in this submission for the sake of completeness.

Electromotive drug administration into body cavities has been in existence for more than 80 years. In 1905 Stanger (U.S. Pat. No. 791,730) described "Electrical Mouth Baths"; then followed Cool (U.S. Pat. No. 873,021) in 1907 with an "Electrotherapeutic syringe" and Warwick in 1938 (U.S. Pat. No. 2,123,980) with "Therapeutic Treatment". During the 1970's and early 1980's several relevant patents were issued in the then USSR (SU Nos. 322, 202; 527, 812; 532, 890; 746, 427; 825,095; 843,999; 876,138; 1,005,796; 1,064, 956), Nashef et al. (U.S. Pat. No. 4,776,349) described an iontophoretic "Tubular Device", while Davis et al. (U.S. Pat. Nos. 4,411,648; 5,328,451) and Griffith et al. (U.S. Pat. No. 5,234,408) demonstrated the antimicrobial effects of electric current in physiological fluids. Patents have been issued in the name of Thiel which claim iontophoresis of certain heterocyclic compounds in the treatment of bladder cancers (German patent No. DE 38 09 814 C1 and U.S. Pat. No. 5,002,956) and Feiring describes "Internal Tissue Medication Permeating Apparatus and Method" (International Patent No. WO 91/16945 and U.S. Pat. No. 5,236,413). Shapland et al. (U.S. Pat. No. 5,286,254) evolved a tubular device with a semipermeable membrane for drug administration to internal organs. Recently, patents have been issued in the name of Stephen et al. which disclose intracorporeal iontophoresis, the treatment of schistosomiasis, localisation and treatment of bladder cancer and treatment of catheter-related infections (U.S. Pat. Nos. 5,222,936; 5,232,441; 5,301,688; 5,401,239). From the same group, Rossi et al. have submitted the patent application No. 08/237,672, now U.S. Pat. No. 5,486,160, for Device for the Combined Electropharmacological Treatment of the Bladder and the Prostatic Urethra.

SUMMARY OF THE INVENTION

It is one of the principal objects of the present invention to provide a novel method of treating pathology of the prostate gland causing acute urinary outflow obstruction and thereby avoid the necessity of surgical treatments.

It is another object of this invention to provide localised higher levels of drugs to targeted tissues which obstruct the urinary outflow system, than can be achieved by conventional drug administration, and to maintain these preferably high tissue levels over therapeutic periods of time.

It is further another object of this invention to provide a urethral catheter for the purpose of confining active treatment electrodes within specified pathological regions associated with the prostate gland.

It is still another object of this invention to provide a urethral catheter to achieve simultaneous treatments of pathological prostatic structures protruding into the bladder and of pathological prostatic structures associated with the prostatic urethra.

It is yet another object of the invention to accelerate administration of locally infused drugs through the relatively impermeable urothelial membrane and into adjacent diseased tissues thereby attaining the desirable goal of high drug concentrations within specified pathological tissues and minimum systemic concentrations of potentially toxic drugs.

Other objects of the present invention will become manifest from a consideration of the specification, accompanying drawings and appended claims.

DETAILED DESCRIPTION OF THE INVENTION

With the foregoing and other objects in view, while taking the aforementioned boundary conditions into consideration, there is provided, in accordance with the invention, a device for treating an acute urinary outflow system obstruction comprising a catheter having a flexible tubular body including a plurality of openings for connection to the tissues, preferably placed at its median and distal portion, at least an elastic sealing device, and an internal ridge, said catheter being internally provided with an electrode having a proximal insulated portion and a distal uninsulated portion.

Said catheter has a distal portion proximate to its tip, which in use protrudes within the bladder wall, a median portion which in use is located along the urethra and a proximal portion proximate to its inlet and which in use is placed outside the body cavity.

According to an embodiment of the present invention said elastic sealing device is arranged circumferentially around the catheter tubular body and preferably comprises a first retaining balloon, more preferably of 3–10 ml, placed between the median and distal portions of the catheter. According to another embodiment of the invention a second retaining balloon is provided, being preferably of 2–4 ml and circumferentially mounted between the proximal and median portions of the catheter.

In accordance with a further feature of the invention said internal ridge is placed between the median and distal portions of the catheter, preferably in juxtaposition of the first retaining balloon, in order to be positioned during use at the bladder neck.

According to another aspect of the present invention, the electrode is provided at its uninsulated tip with a non-conductive disc, preferably of diameter approximating the internal diameter of the catheter, in order to abut against the catheter ridge to form a loose seal.

In accordance with a further embodiment of the invention, the electrode within the tubular body (i.e. the hollow part) of the catheter is bifurcated in a tubular core portion and in an uninsulated spiral arm. The tubular core portion has a proximal insulated portion and a distal uninsulated portion. The first portion extends insulated up to the level of said internal ridge, and thereafter continues in the uninsulated portion along the catheter distal portion. The uninsulated spiral arm is placed within the median portion of the catheter, ends at level of the catheter internal ridge and preferably has a diameter which is approximately equal to the internal diameter of the catheter.

Preferably, said distal uninsulated portion of the tubular electrode, with particular reference to the bifurcated type, is made of Shaped Metal Alloys (SMA) and more preferably consists in an copper-zinc-aluminum-nickel (CZAN) alloy.

The Shaped Metal Alloys are alloys that can be so fabricated that they are very malleable and flexible prior to reaching a specified temperature, but once this temperature is attained they will assume specified shapes, or angles in the case of tubular structures. These alloys are malleable prior to reaching body temperature and once inserted into the body cavity they assume specified (predetermined) angles. In particular, in order to treat an enlarged median lobe the uninsulated tubular portion of the electrode is made of a SMA (for example a nickel-titanium alloy) which is able to resume preferably an angle of 45° to its axis within the bladder cavity (37.5° C.), whereas in order to treat areas associated with the bladder neck and a protruding transitional zone adenoma, a catheter is used which is able to resume within bladder cavity an angle preferably of 135–145° to its axis.

According to another aspect, the device of the present invention provides a method of treating acute urinary outflow obstruction, due to pathology of the prostate gland, by localised electromotive drug administration comprising:

inserting a catheter portion respectively along an urethra and inside a bladder cavity, said catheter portion comprising a plurality of openings, at least an elastic sealing device and an internal ridge;

draining said bladder of urinary contents;

inserting an electrode connected to an external electrical power source inside said catheter, said electrode comprising a proximal insulated portion extending from said external power source to a point located within said catheter and a distal uninsulated portion extending within the catheter;

infusing via said catheter an electrically-conductive drug solution for treating prostate diseases;

placing in contact with a suitable skin location a secondary electrode also connected to said external power source;

supplying an electrical current from said power source to said electrodes.

Infusion of a drug(s) solution into the catheter of the invention results in this solution passing through the catheter holes into the prostatic urethra. Application of electric current of appropriate polarity accentuates administration of the drug(s) through the urothelium and the prostatic capsule, at level of the obstruction of the urinary system. Accordingly, a high drug concentration to the targeted tissues is achieved, avoiding general side-effects due to the systemic administration.

While performing the therapeutic method of the invention, drug(s) are administered for treating prostate diseases selected from the group comprising analgesic, anti-inflammatory, antibiotics, α adrenergic blocking, antiandrogen, anticancer, hemostatic, detrusor muscle stimulating drugs and mixtures thereof.

According to one aspect of the invention, the intensity of the electric current supplied from the power source to the electrodes is preferably of 10 to 40 mA, preferably supplied for time periods ranging from 5 to 60 minutes.

BRIEF DESCRIPTION OF THE DRAWINGS

The method of treatment and the device for performing it, according to the present invention, together with additional objects and advantages thereof, will be best understood from the following description of specific embodiments when read in connection with the accompanying drawings, wherein.

DESCRIPTION OF THE PREFERRED EMBODIMENTS

Figure 1:
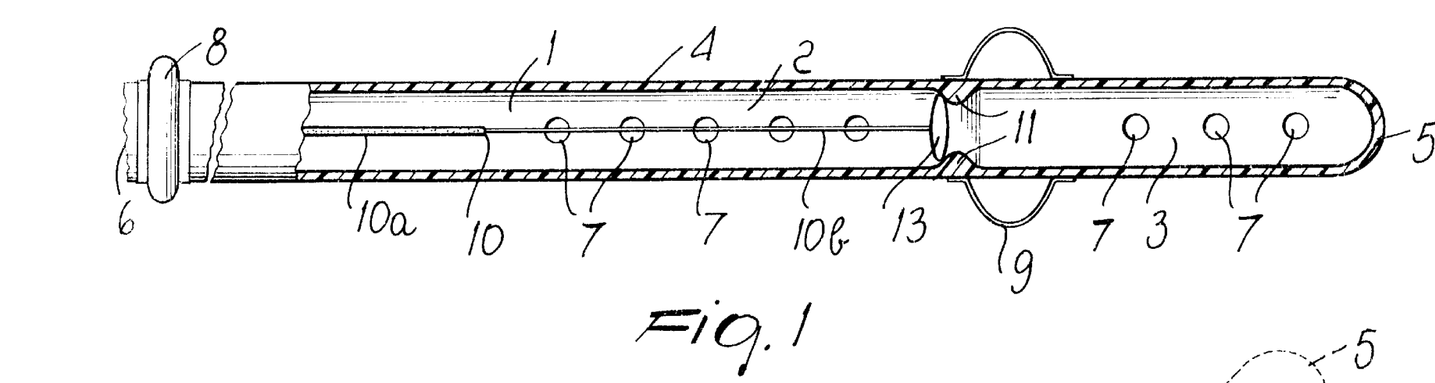
FIG. 1 is a cross-sectional view of the catheter for performing the method of the invention, containing a prostatic urethral electrode and having elastic sealing means.

FIG. 1 illustrates an embodiment for application of the method of the present invention to patients whose acute urinary obstruction is due to prostatic obstruction.

Catheter 1 has a tubular shape with a flexible structure, and a blunt soft tip 5, which in use protrudes inside the bladder cavity of the patient to be treated. Said catheter is made of a soft, flexible, non-irritant, non-conductive material, preferably consisting of silicon, and has an external diameter of 5 mm and an internal diameter of 3 mm. At its proximal end 6 the catheter 1 has a connector with a plurality of inlets of a known type and thus not shown.

Along the wall 4 of the catheter 1 there is a plurality of openings 7 placed at its middle portion 2 and proximate to its distal portion 3.

Circumferentially mounted retaining balloons 8 and 9 are applied in a traverse section of the tubular body of the electrode 1 both at the beginning of its middle portion 2 and at the beginning of its distal portion 3.

Figure 3:
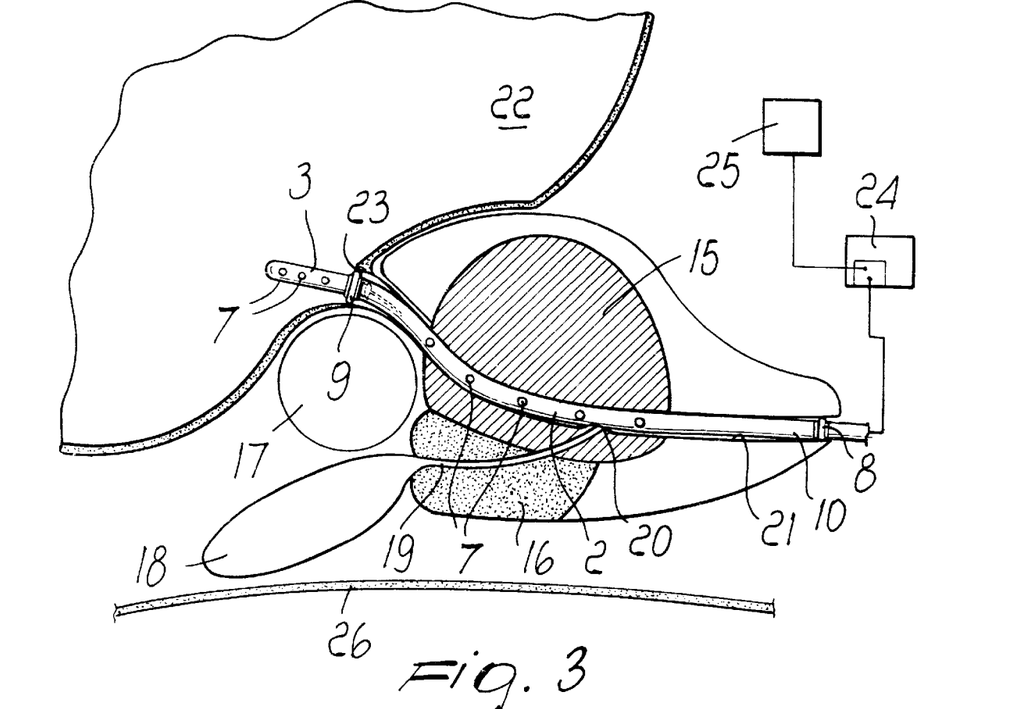
FIG. 3 is a schematic side view of a prostate gland and bladder, showing a catheter inserted along the prostatic urethra and bladder to perform the method of the present invention.

Balloons 8 and 9 illustrated in their inflated state, are positioned in the present method, respectively at the level of the distal end of the prostatic urethra and at the level of the bladder neck (as shown in FIG. 3) of the patient to be treated, in order to seal the portion of the urinary outflow system which is obstructed.

An internal ridge 11 extends around the full circumference of the internal wall 4 of the catheter 1, said ridge 11 functioning both as a guard and a seal for the electrode 7.

A stem-like electrode 10 passes inside the catheter. Said electrode 10 has an insulated portion 10a extending from the power source (not shown) to the middle portion 2 of the catheter 1 and an uninsulated (core) portion 10b which continues from the insulated portion 10a to the internal ridge 11. The uninsulated portion 10b is provided, at its distal end, with a thin, slightly flexible, non-conductive plastic disc 13 having a diameter approximating the internal diameter of the catheter and which abuts against the catheter ridge 11 to form a loose seal.

Figure 2:
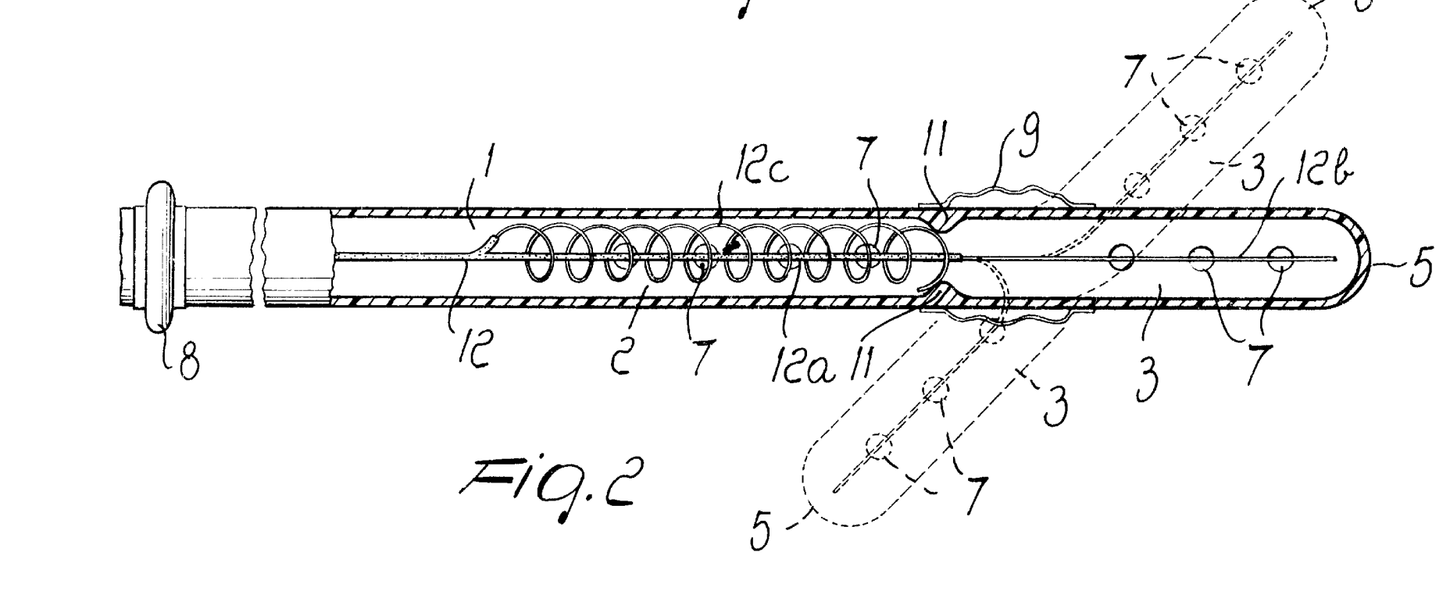
FIG. 2 is a cross-sectional view of a further embodiment of the catheter of the invention containing a bifurcated electrode and having elastic sealing means.

Referring to FIG. 2, an alternative embodiment is illustrated for application of the method of the present invention to treat prostatic intrusions into the bladder cavity which obstruct urine outflow.

Catheter 1 is similar to the type referred to in FIG. 1, has a tubular form, is made of a soft, flexible, non-conductive material, such as silicon, and has a balloon control channel of a known type and thus not shown. This channel is separated from the main hollow part of the tubular catheter 1 and is used to control both the balloon 8, depicted in its inflated state, and the balloon 9, depicted in its deflated state.

A plurality of openings is located only at the level of the distal portion of the catheter 1, in order to perform the electromotive administration of drug solution to the target tissue.

The tip 5 of the catheter 1 is rounded in order to pass easily through the bladder neck without causing damage to the urethral tissues.

A specific bifurcated urethral-bladder electrode 12 is inserted into the hollow part of the catheter 1. Said electrode has a tubular core portion 12a extending from the external power source to the tip 5 of the catheter. The length of said tubular core portion extending from the power source to the level of the ridge 9 is sheathed in an insulating plastic material; the length 12b of the electrode portion extending from the catheter ridge to the tip of the catheter 9 is uninsulated and is made of an SMA composed of copper, zinc, nickel, coated with a thin layer, preferably of 3 microns, consisting of silver or gold.

The memory metal section of the uninsulated portion 12b is made to resume specific angles of either 45° or 135° to the axis of the electrode at temperatures of $\geq 35°$. This result can be achieved by inserting a catheter containing a cool malleable electrode followed by infusion of warm fluid $\geq 36°$ C. or more simply by drainage of urine at body temperature (i.e. 37° C.).

An uninsulated spiral component 12c, the diameter whereof approximates the internal diameter of the catheter, branches from the sheathed core section of the elctrode 12 and travels the full length of the middle portion 2 of the catheter, terminating at the catheter ridge 11. The material of this uninsulated spiral section consists of copper.

FIG. 3 illustrates the embodiment of FIG. 1 as it may be used in the practical execution of the method of the present invention.

The depicted prostate gland 14 has an enlarged transitional zone 15, a normal central zone 16 and an enlarged median lobe 17.

In the enlarged transitional zone 15, an adenoma (not shown) compresses and obstructs the urinary outflow system, with particular reference to the prostatic urethra. The present figure furthermore shows the rectal wall 26 and a seminal vesicle 18 located above the rectal wall, with its ejaculatory duct 19 leading to the level of the verumontanum region 20.

The use of the present embodiment of the invention provides for the insertion of the catheter 1 in the urinary outflow system of a patient in need of the treatment, in a conventional manner until its distal portion 2 reaches the inside of the bladder 22.

Conventionally, the direction towards and within the bladder is termed "proximal", whereas the one along the urethra towards the tip of the penis is termed "distal".

During the use of the device according to the invention, the catheter 1 has its middle portion 2 placed along the prostatic urethra 21 and its distal portion 3 within the bladder cavity 22. A balloon 9 fixed proximate to the bladder neck 23 is inflated to delimit and isolate the bladder cavity 22. A plurality of openings 7 is located both in the distal portion 3 and in the middle portion 2 of the catheter 1. The plurality of openings 7 of the middle portion 2 of the catheter 1 is placed at the enlarged transitional zone 15 of the prostate gland 1, wherein there is an adenoma which represents the target tissue in need of the therapeutic treatment. A retaining inflated balloon 8 is placed at the distal end of the prostatic urethra, in order to close the distal passage section of the urethra during the performance of the method of the present invention.

A stem-like electrode 10 passes inside the hollow tubular body of the catheter 1 and is divided into an uninsulated distal portion having at its end a non-conductive disc 13, and into a proximal insulated portion 10a connected to the external power source 24. The uninsulated portion 10b of the electrode extends along the catheter middle portion 2 wherein openings are provided, in order to realize an appropriate current flow at the transitional zone 15 of the prostate gland 14 which needs to be treated. The external power source 24 is also connected to a secondary dispersive electrode 25 placed on some convenient area of the skin of the patient (for example upon the abdominal wall 26) to be treated with the method of the invention.

The treatment method of the invention provides for drainage of the bladder urinary contents, by means of the openings 7 placed in the distal portion 3 of the catheter 1, and for insertion along the hollow cavity of the catheter 1 of the above mentioned electrode to the level of the bladder neck where said electrode terminates in a disc of electrically non-conductive material which abuts against the catheter ridge.

An electrically-conductive drug solution is then instilled into the prostatic section of the urethra via said catheter 1, the electric power source 24 is switched on, activating the ions contained in the drug solution, thereby producing the therapeutic effect in the target tract of the urinary outflow system wherein the obstruction is localised.

The depicted power source 24 is of the current-controlled type, preferably a battery-powered source. The current waveform incorporates constant DC, pulsed DC and preferably a timing device (not shown) to allow reversal of polarity with a frequency of 5–20 minutes. The envisaged electric currents have an intensity of 5–10 mA.

Figure 4:
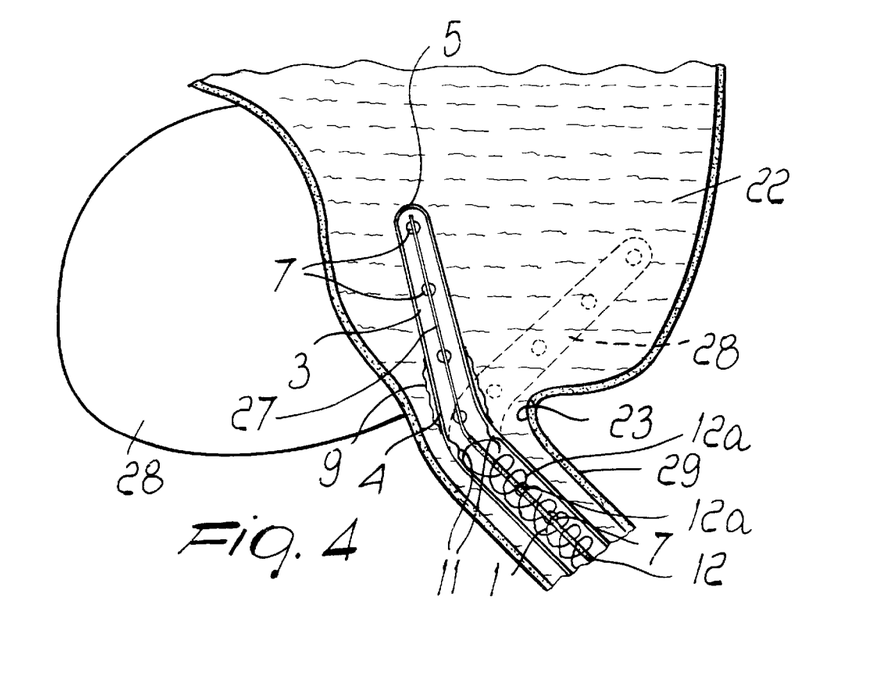
FIG. 4 is a schematic cross-sectional view of another embodiment of the catheter of the invention, positioned within the bladder.

FIG. 4 refers to a further embodiment of the method of the present invention. Catheter 1 of the device of the invention is depicted both placed in a correct position 27, in juxtaposition to a pathological middle lobe 28 of a prostate gland, as compared to a normal bladder wall, and in an incorrect position 28 (broken lines).

Catheter 1 is depicted with four openings placed at the level of its distal portion 3 and a plurality of openings in the middle section to permit both the drainage of the urinary content and the electromotive administration of drug(s). A retaining balloon 9 in its deflated state is fixed on the external wall 4 of the catheter 1, at level of the bladder neck 23.

Catheter 1 is provided with a ridge 11 of height 0.5 mm and width 0.5 mm extending around the full circumference of the internal wall 4 and located at the level of the proximal end 29 of the prostatic urethra just distal to the retaining balloon 9.

Said (bifurcated) electrode 12 extending from the external power source (not shown) to the tip 5 of the catheter 1, positioned inside the bladder cavity 22, is inserted within the tubular body of the catheter 1.

The core length 12a of the electrode extending from the power source to the level of the catheter ridge 11 is sheathed in an insulating plastic material, whereas the spiral arm 12c is uninsulated.

The conductive material of the tubular core section of the insulated portion 12b of the electrode and of the spiral arm 12c consists of copper.

The spiral arm 12c of the electrode (12) is properly positioned so as to treat a pathological transitional zone (not shown).

The distal portion 3 of the catheter 1 is placed within the bladder cavity 22 in a specific position in order to treat the enlarged median lobe 28 which can obstruct the urinary outflow system, otherwise the great proportion of electric current may be misdirected therapeutically. The catheter-electrode is illustrated angled at 45° to its axis which offers the best chance of success for treating by EMDA an enlarged median lobe of the prostate.

The material of which the uninsulated electrode extending from the catheter ridge 11 to the tip of the catheter is made is an SMA composed of copper, zinc, aluminium, nickel and advantageously it is also coated with a thin layer (3 microns) of silver or gold. This material is fabricated in order to resume a specific angle of either 45° or 135° to the axis of the electrode at temperatures $\geq 35°$.

In the present embodiment, this objective is achieved during the initial phase of the method consisting in the drainage of urine at body temperature (37° C.) by means of the openings 7 placed along the distal portion of the catheter. During this initial phase, electrode 12b resumes a specific angle of approx. 45° to the axis of the insulated portion 12a and is then positioned within the bladder cavity under ultrasound control in the correct position as illustrated, in order to permit the performing of the electromotive drug administration to both the transitional zone and the enlarged median lobe 28 of the prostate gland, which causes the obstruction 30 of the urinary system, at the level of the bladder neck 23.

The current flow applied to the bifurcated electrode 12 is preferably of 20–30 mA.

By the electromotive drug administration of the present invention, a specific ion flow is directed to the target sites, providing for a high drug concentration only in proximity of the pathological tissues.

The method and device of the present invention provide numerous advantages. By utilizing the urethral catheter of the invention, specific internal locations of a patient may be targeted for treatment with a particular medication. Furthermore, the permeation of the medication into the body pathological tissue avoids an excessive concentration of medication to the patient.

The analgesic drugs useful in the present method are preferably local anaesthetic agents, more preferably selected from the group comprising lidocaine, mepivacaine, bupivacaine, ropivacaine and mixtures thereof, preferably administered in concentrations ranging 0.3–1% by weight. These agents can be administered in mixture with epinephrine, to a concentration ranging 1/200,000–1/50,000, in order to achieve a prolonged effect.

The anti-inflammatory drugs (both steroidal and non-steroidal drugs) useful in the present method are preferably selected from the group comprising dexamethasone, betamethasone, ketorolac, diclofenac and mixtures thereof. In order to achieve an high anti-inflammatory effect, the steroidal drugs are administered in concentrations preferably ranging 0.08%–0.3% by weight, whereas the non-steroidal drugs are administered in concentrations preferably ranging 0.15%–1.0% by weight.

The α adrenergic blocking agents, useful in the practice of the invention, are preferably selected from the group comprising phenoxybenzamine, phentolamine, prazosin, terazosin, doxazosin, trimazosin, alfuzosin and mixtures thereof. These agents are of particular value in causing profound relaxation of the internal sphincter and related muscular tissue, in particular when administered at a concentration of 0.025%–0.1% by weight, preferably in a physiological electrolyte solution of osmolarity of 150–310 mOsm. Said α blocking agents can also be infused as citrate salt solution, preferably having a concentration ranging from 1 to 3% by weight.

The performing of the method of the invention allows the local administration of a readily available amount of antibacterial agents preferably selected from the group comprising ampicillin, cephalothin, cephapyrin, cephazolin, cephalexin, gentamycin, netilmicin, norfloxacin, ciprofloxacin, trimethoprim-sulfamethoxazole, ciclopirox and mixtures thereof.

The local administration by EMDA of antimicrobial agents is very useful in destroying micro-organisms sheltered in privileged sites. This effect is particularly benefical in case of infective prostatitis where systemic antimicrobial therapy is not satisfactory. In particular, the method of the invention is performed by infusing a solution containing at least one among ampicillin, cephalothin, cephapyrin, cephazolin, cephalexin and ciclopirox, at concentrations preferably of 0.1–3% by weight, using an electrode of negative polarity. According to another embodiment, at least one drug selected among gentamycin, tobramycin, netilmycin, norfloxacin, ciprofloxacin and trimethoprim/sulphamethoxazole is administered. Said drugs are administered preferably at concentrations ranging 1–3% by weight and using an electrode of positive polarity. According to a further embodiment, specific antimicrobial combinations consisting of a mixture of either ampicillin, cephalothin, cephalexin, cephapyrin, cephazolin and either gentamycin, tobramycin, netilmycin, are administered by supplying an alternating current of frequency of preferably 1/5–20 min.

According to yet another aspect, the method of the present invention allows the local administration of antiandrogen agents, advantageously selected from the group comprising cyproterone acetate, flutamide, finazteride and mixtures thereof. Said antiandrogen agents are administered by using an electrode of positive polarity, preferably solubilised to a 0.5–2% solution in ethanol, said ethanol solution of drug being admixed in an aqueous electrolyte solution, preferably in a 1/10 ratio. Said electrolyte solution preferably consists of a physiological electrolyte solution of osmolarity 150–310 mOsm, or of a citrate salt solution of concentration of 1 to 3% by weight.

The method of the present invention furthermore allows the treatment of cancerous forms located at the prostate gland, which can obstruct the urinary outflow system. In fact, since the urothelium tolerates EMDA of anticancer drugs, high localised levels are achievable without systemic side-effects. Preferably said anticancer drugs are selected from the group comprising doxorubicin, epirubicin, mitoxantrone, bleomycin, mitomycin C and mixtures thereof, advantageously administered at a concentration of 0.01–0.1% by weight, in a physiological electrolyte solution or a citrate salt solution, using an electrode of positive polarity.

According to a further aspect, the present invention provides the local administration of hemostatic agents in order to treat hemorrhages which can occur from a long standing distended bladder wall. Preferred hemostatic agents are desmopressin, phytadione, conjugated estrogen, aminocaproic acid, aprotinin and thrombin. These agents are preferably administered in concentrations ranging from 1 mcg/ml–1 g/100 ml, except aprotinin and thrombin which are preferably administered in concentrations ranging from 10 IU/100 ml–10,000 IU/100 ml.

According to another aspect, the present method provides the administration of cholinergic agents, preferably selected from the group comprising methacoline, carbachol, bethanecol and mixture thereof. Said drugs are very useful in assisting an attenuated bladder containing a volume of drug solution to contract. If the first catheter balloon is deflated, the contracting bladder will force the drug solution contained in its cavity into the prostatic urethra and EMDA of the drugs into the prostatic urethra is achieved with the bladder acting as a drug reservoir.

To maintain these desirably high tissue levels over therapeutic periods of time there are several options, which depend upon the individual patient's general response to a particular drug and the pharmacokinetics of the drug(s) used: repeated EMDA therapies alone which is the only possible option with local anaesthetic drugs, with anticancer drugs and the only desirable option with hemostatic and anti-inflammatory drugs; repeated EMDA therapies, each lasting 20–60 minutes, combined with low dose systemic therapies which is a logical choice for many antibiotics and α adrenergic blocking agents; repeated EMDA therapies with moderate dosage systemic therapy, which is the best option for anti-androgen drugs.

Finally it must be noted that the quantity of drug recommended for each EMDA treatment never exceeds the total daily dose of that drug were it to be administered systemically. The reason is that, although ENMA per se results in far less than these quantities being administered into tissues (Faraday's Law), untoward events are always possible: rupture of the bladder or a major vein can result in absorption of most of the infused fluids and drugs contained therein. Thus, although electromotively disadvantageous with the low concentration of some drugs, this rule is a good safety precaution for patients.

All salts of local anaesthetic drugs (e.g. lidocaine hydrochloride) and epinephrine are positively charged and the concentrations used are sufficient to allow efficient conduction of at least a 30 mA electric current. Salts of corticosteroids and NSAID's (non-steroidal anti inflammatory drug) are negatively charged but, as shown by Petelenz et al., it is possible to administer these agents electromotively in combination with local anaesthetic drugs against their coulombic gradients.

The α adrenergic blocking agents are available as positively charged salts, but the low concentrations required for safety reasons make it desirable to infuse these drugs in either a physiological electrolyte solution or a citrate salt (sodium or potassium citrate) solution.

The aforementioned anticancer agents are available as positively charged salts and are administered electromotively using an electrode of positive polarity.

Among the antimicrobial agents selected, the β lactam antibiotics and ciclopirox are negatively charged. The aminoglycosides and quinolones are positively charged. With the exception of ciclopirox, all can be infused in sufficiently high concentrations to conduct 30 mA current efficiently, and ciclopirox itself will always be infused in conjunction with a β lactam antibiotic.

The antiandrogen drugs pose a problem in that their solubility in water is very low. They are, however, readily soluble in ethanol and, so solubilised, they can be infused in an electrolyte or citrate salt solution and then administered by electrophoresis.

The hemostatic drugs selected display a very wide range in their molecular size and so the concentrations infused, preferably ranging from 10 to 10000 IU, are listed as both in m/v and International Units/Volume (IU/V).

The following example is only illustrative of the present invention. Several modifications and alternatives may be devised by those skilled in the art without departing from the spirit and the scope of the present invention.

EXAMPLE

Seven male patients age 61–77 years afflicted with multiple tumors of the bladder and a modest degree of prostatic obstruction were treated with EMDA of the local anaesthetic drug, lidocaine, and the vasoconstrictor, epinephrine.

A specially fabricated catheter with perforations extending from the intravesical tip approximately to the distal end of the prostatic urethra and a 3 ml bladder neck balloon, according to the invention, was selected.

There was inserted into the catheter an electrode of an insulated tubular configuration extending from the external power source and then terminating in 8 cm of uninsulated spiral which is the approximate distance from the centre of the bladder (where the catheter tip is sited) to the distal end of the prostatic urethra.

The catheter was inserted, balloon inflated, the bladder was drained and 150 ml of lidocaine 2% with 1/100,000 epinephrine was infused intravesically through the catheter. Electric current of 15–20 mA intensity was applied through the catheter-electrode. After 11 minutes the catheter balloon was deflated, bladder contents drained out the catheter at 3–4 ml/min and current was maintained at 15–20 mA for a further 4 minutes. After 15 minutes of treatment the current ceased, the bladder was drained and the whole process was repeated.

By performing the above treatment method two objectives have been achieved: to render the bladder wall analgesic and to render the prostatic urethra and surrounding structures (prostatic capsule and gland) analgesic.

All patients easily tolerated Transurethral Resection (TUR) of a plurality of bladder tumors with diathermy and cautery, a procedure normally performed under general or regional anaesthesia, and a bladder neck incision (BNI). A BNI, as the name implies, is a surgical incision about 1–2 cm deep through the bladder neck and running the length of the prostatic urethra. It is a rapid, minimally invasive technique for relief of minor obstruction at the bladder neck when spasm of smooth muscle plays an important role.

Three important objectives were achieved: analgesia of the required regions; an anti-inflammatory effect (epinephrine) as noted by the pallor visualised though the endoscopes and on the video screen; the bladder acting as a reservoir and supplying drug solution to the prostatic urethra when the catheter balloon was deflated. Nevertheless, the clinical situations were over-simplified in that the prostate glands were only modestly enlarged and there was no acute obstruction associated with edema, inflammation, infection or cancer.

What is claimed is:

1. A method of treating acute urinary outflow obstruction, due to pathology of the prostate gland, by localised electromotive drug administration comprising:

inserting a catheter portion respectively along an urethra and inside a bladder cavity, said catheter portion comprising a plurality of openings, at least an elastic sealing device and an internal ridge;

draining said bladder of urinary contents;

inserting an electrode connected to an external electrical power source inside said catheter, said electrode comprising a proximal insulated portion extending from said external power source to a point located within said catheter and a distal uninsulated portion extending within the catheter;

infusing via said catheter an electrically conductive drug solution for treating prostate diseases;

placing in contact with a suitable skin location a secondary electrode also connected to said external power source;

supplying an electrical current from said power source to said electrodes.

2. A method according to claim 1, wherein said at least an elastic sealing device comprises a retaining balloon.

3. A method according to claim 2, wherein said elastic sealing device consists of a first retaining balloon placed between the median and distal portions of said catheter and a second retaining balloon placed between the proximal and median portions of said catheter.

4. A method according to claim 1, wherein said plurality of openings is placed at the median and distal portions of the catheter.

5. A method according to claim 1, wherein said internal ridge is placed between the median and distal portions of the catheter.

6. A method according to claim 5, wherein said internal ridge extends around the full circumference of the catheter internal wall.

7. A method according to claim 1, wherein said drug for treating prostate diseases is selected from the group consisting of analgesic, anti-inflammatory, antibiotics, α adrenergic blocking, antiandrogen, anticancer, hemostatic, detrusor muscle stimulatory drugs and mixtures thereof.

8. A method according to claim 7, wherein said drug for treating prostate diseases consists of a mixture of an anti-inflammatory and an analgesic drug.

9. A method according to claim 7, wherein said drug for treating prostate diseases is a mixture of a local anaesthetic agent, a vasoconstrictor agent, and an anti-inflammatory drug.

10. A method according to claim 9, wherein said anaesthetic agent is selected from the group consisting of lidocaine, mepivacaine, bupivacaine, ropivacaine; said vasoconstrictor drug is epinephrine, said anti-inflammatory drug is a corticosteroid selected from the group consisting of dexamethasone and betamethasone.

11. A method according to claim 7, wherein said α adrenergic blocking drug is selected from the group consisting of phenoxybenzene, phentolamine, prazosin, terazosin, doxazosin, trimazosin, alfuzosin and mixtures thereof.

12. A method according to claim 11, wherein said α adrenergic blocking drug is administered in a physiological electrolyte solution of osmolarity of 150 to 310 mOsm at a concentration of 0.025% to 0.1% by weight.

13. A method according to claim 11, wherein said α adrenagic blocking drug is administered at a concentration of 0.025 to 0.1% by weight in a citrate salt solution having a salt concentration of 1 to 3% by weight.

14. A method according to claim 7, wherein said antibiotic is selected from the group consisting of ampicilin, cephalotin, cephapyrin, cephazolin, cephalexin, gentamycin, tobramycin, netilmycin, norfloxacin, ciprofloxacin, trimethoprim-sulfamethoxazole, ciclopirox and mixtures thereof.

15. A method according to claim 7, wherein said antibiotic is selected from the group consisting of ampicillin, cephalothin, cephapyrin cephazolin, cephalexin and ciclopirox and is electromotively administered at a concentration of 0.1 to 3% by weight apply a negative polarity.

16. A method according to claim 7, wherein said antibiotic is selected from the group consisting of gentamycin, tobramycin, netilmycin, norfloxacin, ciprofloxacin, trimethoprim-sulfamethoxazole and is electromotively administered at a concentration of 1 to 3% by weight applying a positive polarity.

17. A method according to claim 7, wherein said antibiotic is a mixture of at least an antibiotic selected from the group consisting of ampicillin, cephalotin, cephalexin, cephapyrin, cephazolin and at least an antibiotic selected from the group consisting of gentamycin, tobramycin, netilmycin, said mixture being electromotively administered by means of an alternating current of frequency of 20 sec. to 20 min.

18. A method according to claim 7, wherein said drug for treating prostate diseases is an antiandrogen drug selected from the group consisting of cyproterone acetate, flutamide, finazteride and mixtures thereof.

19. A method according to claim 7, wherein said drug for treating prostate diseases is an anticancer drug selected from the group consisting of doxorubicin, epirubicin, mitoxantrone, bleomycin, mitomycin C and mixtures thereof.

20. A method according to claim 7, wherein said drug is a hemostatic drug selected from the group consisting of desmopressin, phytadione, conjugated estrogen, aminocaproic acid and mixtures thereof.

21. A method according to claim 7, wherein said drug is a detrusor-muscle stimulatory drug selected from the group consisting of methacoline, carbachol, bethanechol and mixtures thereof.

22. A method according to claim 1, wherein said electrically conductive drug solution is an aqueous solution.

23. A method according to claim 1, wherein said electrical current is of 10 mA to 30 mA.

24. A method of treating acute urinary outflow obstruction, due to pathology of the prostate gland, by localised electromotive drug administration comprising:

inserting along an urethra a catheter portion, said catheter portion comprising a plurality of openings, a first retaining balloon placed between a distal and a median catheter portions and a second retaining balloon placed between the median and a proximal catheter portions, and an internal ridge located at level of said first balloon;

placing the first retaining balloon at level of a bladder neck and the second retaining balloon at level of a distal end of an urethra of a patient in need of treatment;

draining said bladder of urinary contents and inflating said balloons;

inserting said electrode having at its tip a disc of non-conductive material, along the catheter urethral portion until said tip abuts against said ridge;

infusing via said catheter an electrically conductive drug solution for treating prostate diseases;

placing in contact with a suitable skin location a secondary electrode also connected to said external power source;

supplying an electrical current from said power source to said electrodes.

25. A method according to claim 24, wherein said ridge extends around the full circumference of the catheter internal wall.

26. A method according to claim 25, wherein said disc is of a diameter approximately equal to the internal diameter of the catheter, to form a loose seal with said ridge.

27. A method of treating acute urinary outflow obstruction, due to pathology of the prostate gland, by localised electromotive drug administration comprising:

inserting along an urethra a catheter portion, said catheter portion comprising a plurality of openings, a first retaining balloon placed between a distal and a median catheter portions and a second retaining balloon placed between the median and a proximal catheter portions, and an internal ridge located at level of said first balloon;

placing the first retaining balloon at level of a bladder neck and the second retaining balloon at level of a distal end of an urethra of a patient in need of treatment;

draining said bladder of urinary contents and inflating said balloons;

inserting said electrode which is bifurcated in a tubular core portion having a proximal insulated portion and a distal uninsulated portion which extends along the catheter distal portion, and in an uninsulated spiral portion;

infusing via said catheter an electrically conductive drug solution for treating prostate diseases;

placing in contact with a suitable skin location a secondary electrode also connected to said external power source;

supplying an electrical current from said power source to said electrodes.

28. A method according to claim 27, wherein the uninsulated tubular electrode portion is made of a shaped metal alloy which assumes an angle of approximately 45° to its axis when its temperature exceeds 35° C. and returns to its original form when its temperature is below 35° C.

29. A method according to claim 27, wherein said conductive drug solution is infused at a temperature above 35° C.

30. A method according to claim 27, wherein the uninsulated tubular electrode portion is made of a shaped metal alloy which assumes an angle of approximately 135° C. to its axis when its temperature exceeds 35° C. and returns to its original form when its temperature is below 35° C.

* * * * *